(12) United States Patent
Huijbregts et al.

(10) Patent No.: US 11,419,511 B2
(45) Date of Patent: Aug. 23, 2022

(54) SYSTEM AND METHOD FOR SENSING PHYSIOLOGICAL PARAMETERS

(71) Applicant: KONINKLIJKE PHILIPS N.V., Eindhoven (NL)

(72) Inventors: Laurentia Johanna Huijbregts, Eindhoven (NL); Gerard De Haan, Helmond (NL); Mark Josephus Henricus Van Gastel, Tilburg (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 159 days.

(21) Appl. No.: 16/764,535

(22) PCT Filed: Nov. 13, 2018

(86) PCT No.: PCT/EP2018/080990
§ 371 (c)(1),
(2) Date: May 15, 2020

(87) PCT Pub. No.: WO2019/096753
PCT Pub. Date: May 23, 2019

(65) Prior Publication Data
US 2020/0345252 A1    Nov. 5, 2020

(30) Foreign Application Priority Data

Nov. 16, 2017 (EP) .................................... 17202096

(51) Int. Cl.
*A61B 5/024* (2006.01)
*A61B 5/1455* (2006.01)
(Continued)

(52) U.S. Cl.
CPC ...... *A61B 5/02416* (2013.01); *A61B 5/14551* (2013.01); *A61B 5/318* (2021.01);
(Continued)

(58) Field of Classification Search
CPC . A61B 5/1455; A61B 5/14551; A61B 5/6823; A61B 5/7221; A61B 5/7253
See application file for complete search history.

(56) References Cited

U.S. PATENT DOCUMENTS 4,802,486 A   2/1989 Goodman et al.
5,313,941 A * 5/1994 Braig ................. A61B 5/14532
                                                600/322
(Continued)

FOREIGN PATENT DOCUMENTS

WO    2017055218 A1    4/2017

OTHER PUBLICATIONS

International Search Report and Written Opinion, International Application No. PCT/ EP2018/080990, dated Feb. 4, 2019.
(Continued)

*Primary Examiner* — Eric F Winakur

(57) ABSTRACT

The invention provides a physiological parameter sensing system (50) and method in which physiological information indicative of at least one physiological parameter is derived. The approach of the invention is based on constructing multiple pulse signals from different weighted combinations of at least two detection signals, derived from detected electromagnetic radiation directed onto or through a subjects skin region. The weightings are based on different of a set of various blood volume pulse vectors. A quality indication value is derived for each generated pulse signal, where this is based on a derived relationship between an obtained heart rate signal for the patient and the pulse signal. The blood volume pulse vector resulting in the pulse signal having the highest quality indicator value and/or from the derived pulse signal itself is used to derive the physiological parameter information.

23 Claims, 4 Drawing Sheets

(51) Int. Cl.
   *A61B 5/00*      (2006.01)
   *A61B 5/318*     (2021.01)

(52) U.S. Cl.
   CPC .......... *A61B 5/6823* (2013.01); *A61B 5/7221*
            (2013.01); *A61B 5/7253* (2013.01); ***A61B
         5/7278*** (2013.01); *A61B 2562/0219* (2013.01)

(56) References Cited

U.S. PATENT DOCUMENTS

| | | | |
|---|---|---|---|
| 8,335,550 B2 * | 12/2012 | Segman | ............. A61B 5/14546 |
| | | | 600/310 |
| 9,510,775 B2 | 12/2016 | Morren et al. | |
| 2014/0221852 A1 | 8/2014 | Van Slyke et al. | |
| 2017/0112422 A1 | 4/2017 | Hatch | |

OTHER PUBLICATIONS

De Haan, et al., "Improved motion robustness of remote-PPG by using the blood vol. pulse signature", Physiol. Meas. 35, 1913.
Van Gastel, M. et al., "New principle for measuring arterial blood oxygenation, enabling motion-robust remote monitoring", Scientific Reports 6, 2016.

\* cited by examiner

SYSTEM AND METHOD FOR SENSING PHYSIOLOGICAL PARAMETERS

This application is the U.S. National Phase application under 35 U.S.C. § 371 of International Application No. PCT/EP2018/080990, filed on 13 Nov. 2018, which claims the benefit of European Application Serial No. 17202096.8, filed 16 Nov. 2017. These applications are hereby incorporated by reference herein.

FIELD OF THE INVENTION

This invention relates to a system and method for sensing a physiological parameter of a subject, in particular a system and method making use of reflection or transmission of electromagnetic radiation from or through a skin region of a subject's body.

BACKGROUND OF THE INVENTION

Physiological parameters of a person, for example the heart rate (HR), the respiration rate (RR) or the arterial blood oxygen saturation ($SpO_2$), serve as indicators of the current state of a person and as powerful predictors of serious medical events. For this reason, physiological parameters are extensively monitored in inpatient and outpatient care settings, at home or in further health, leisure and fitness settings.

One way of measuring physiological parameters is plethysmography. Plethysmography generally refers to the measurement of volume changes of an organ or a body part and in particular to the detection of volume changes due to a cardio-vascular pulse wave traveling through the body of a subject with every heartbeat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. In addition to information about the heart rate, a PPG waveform can comprise information attributable to other physiological phenomena such as respiration. By evaluating the transmittance and/or reflectivity at different wavelengths (typically red and infrared), the blood oxygen saturation can be determined.

One particularly important physiological parameter measurable using certain varieties of PPG sensor is that of arterial oxygen saturation ($SpO_2$). PPG sensors capable of measuring $SpO_2$ will be referred to as 'SpO2 sensors' in the present disclosure. This is to be understood as a reference to a particular kind of PPG sensor which is able to measure $SpO_2$.

Arterial oxygen saturation is a vital parameter that needs to be monitored continuously in intensive care units and in the operating room. It is also a useful parameter for patient monitoring on the general ward. An $SpO_2$ sensor may be placed on the finger. Other locations for sensor placement are also possible (e.g. forehead, toe, or earlobe), as well as contactless monitoring.

The output of an $SpO_2$ sensor, namely the blood oxygen saturation, is defined as:

$$S_PO_2 = \frac{(HbO)_2}{(HbO)_2 + Hb}$$

where $HbO_2$ is the concentration of hemoglobin having oxygen bound to it and $Hb$ is the concentration of hemoglobin without oxygen bound to it.

SpO2 sensors (as PPG sensors) measure blood volume changes optically; detecting light which has traveled through the skin (and potentially underlying tissue), from which blood volume changes may be determined. $SpO_2$ sensors make use of the absorption of light of at least two wavelengths. The amount of detected light depends on the light absorption. The absorption spectrum of deoxygenated hemoglobin is different from that of oxygenated hemoglobin, allowing $S_pO_2$ to be derived.

This is illustrated in FIG. 1. FIG. 1(A) shows the molar extinction coefficient (y-axis; $cm^{-1} Mole^{-1}$) of oxygenated and deoxygenated hemoglobin as a function of the wavelength of incident light (x-axis; nanometers). Line 22 shows the extinction coefficient for oxygenated blood, and line 24 for do-oxygenated blood. FIG. 1(B) shows pulsatility (y-axis; arbitrary units) of completely oxygenated blood (line 22) and partially (60%) oxygenated blood (line 24) as a function of wavelength (x-axis; nanometers).

The pulsatility of the sensor signal is defined at the time-varying AC part of the signal divided by the constant (or slowly varying) DC component of the signal. The light absorption of (skin) tissue and venous blood contribute to the constant (or slowly varying) "DC" component of the detected light signal, while pulsations in the arterial blood contribute the part of the signal which varies with the cardiac cycle (the "AC" component). $SpO_2$ sensors make use of the pulsatility for at least two wavelengths of light.

The approach is illustrated in FIG. 2 which shows detected light signals at a PPG ($SpO_2$) sensor for each of a red light source (line 28) and an infrared light source (line 30). Arrows 32 and 36 shows the AC amplitude value for each of the red and infrared light signals respectively, and arrows 34 and 38 show the DC values for each of the red and infrared light sources respectively.

In reflective mode, the pulsatility as a function of wavelength (see FIG. 1 (B)) is not only determined by the molar extinction coefficient (and possible specular reflectance), but also by the penetration depth of the wavelength. For example, blue light penetrates the skin only very shallowly and therefore reaches relatively few vessels with pulsatile blood. Red light by contrast penetrates much deeper.

In a traditional SpO2 sensor, the so-called "ratio of ratios" R is used to calculate the $SpO_2$-value. The ratio of ratios R is the relative (AC/DC) pulsatility of one wavelength of sensor light divided by the relative pulsatility of a second wavelength:

$$R = \frac{(AC/DC)_1}{(AC/DC)_2}$$

Typically, red (~660 nm) and infrared (~800 nm, 840 nm, or 940 nm) light is used. $SpO_2$ is calculated from an empirically determined equation, such as $SpO_2=110-25*R$ (%) (depending on the wavelengths used).

One known method is to determine R beat-by-beat, using maximum and minimum values in a single pulse-period to derive AC component amplitude and DC component amplitude—e.g. based on an average of the maximum and minimum values. A further alternative method includes for instance averaging the different light signals over multiple beats, or processing the signals after Fourier transformation.

More recently, a new method has been proposed for deriving a measure of physiological parameters using PPG signals. This known as the "adaptive PBV-method" (APBV) and is described in detail in WO 2017/055218.

In this method, a set of so called blood volume pulse vectors ("$P_{bv}$-vectors"), whose components represent possible relative pulsatilities of optical signals at two or three different wavelength components is used as a basis for extracting pulse-signals from the measured optical signals. In particular, a plurality of pulse-signals may be derived where each is formed as a combination (e.g. linear combination) of the sensed optical signals of different wavelengths, using weightings correlated with one of the set of blood volume pulse vectors.

Quality indicator values are then derived for each generated $P_{bv}$-vector.

The $P_{bv}$ vector which generates the best quality pulse-signal, for instance the pulse signal featuring the highest peak in the normalized power spectrum, is then selected and used to derive arterial oxygenation. This is because presence of the highest peak is an indication of the highest signal to noise ratio (SNR), i.e. highest quality signal.

$SpO_2$ may be derived from the identified highest quality $P_{bv}$ vector by means for instance of a pre-determined lookup table which associates $P_{bv}$ vectors with $SpO_2$ values, or by means of a calibration equation allowing determination of $SpO_2$ based on the $P_{bv}$ vector. A calibration equation might for instance take the form $SpO_2=100-C_1*k$ where $C_1$ is a detection signal value received from the $SpO_2$ sensor and k is number associated with the $P_{bv}$ vector which yields the highest quality signal (e.g. a number of the $P_{bv}$ vector as listed in a table or list).

The method is essentially an indirect means of identifying a blood volume pulse vector which most closely matches the 'true' blood volume pulse vector which characterizes a subject's pulse absent any noise.

This method is robust against artefacts in the signal that have a different relative strength in the wavelength channels, such as a changing contact of the sensor with the subject's skin (for contact sensors) or the body part moving to and from the camera (for remote monitoring).

For accurate determination of $SpO_2$ it is important that the 'best' blood volume pulse vector $P_{bv}$ is chosen, i.e. the one resulting in the highest quality signal. To this end, quality indicator values are determined for each of the pulse signals derived from the different $P_{bv}$ vectors.

One simple and advantageous quality indicator is that of the height value of the highest peak in the frequency spectrum for each pulse-signal.

Each extracted pulse-signal (using a particular $P_{bv}$-vector) may be normalized in the Fourier-domain, such that the sum of the spectral energies equals 1. Following this, the pulse signal exhibiting the highest peak in the frequency plot is identified as the highest quality pulse signal. This is illustrated in FIG. 3 which shows in (A) and (B) two pulse signals derived from different respective blood volume pulse vectors, each signal transformed into the frequency domain. The x-axis represents frequency, and the y-axis represents the magnitude of the frequency components.

It can be seen that pulse signal (A) features the highest peak 42. Hence, signal (A) in this simple example would be selected as the highest quality signal, and the physiological information therefore derived using the blood volume pulse vector from which pulse signal (A) was derived.

Although use of this quality criterion generally leads to good motion robustness, it may become problematic with mobile patients, or with patients who suffer from severe arrhythmias. For such patients, motion artefacts in generated signals remain a significant issue. In addition, in cases where an SpO2 sensor is placed on the chest, signals may contain a significant component corresponding to respiration. These respiratory fluctuations can often be misinterpreted as contributions to the pulse signal, resulting in erroneous measurement of SpO2.

An improved approach to deriving physiological parameters is sought which makes use of the APBV method outlined above, but offering improved accuracy and improved robustness against motion artefacts.

SUMMARY OF THE INVENTION

The invention is defined by the claims.

According to an aspect of the invention, there is provided a physiological parameter sensing system, comprising:

a sensing interface adapted to obtain at least two detection signals derived from detected electromagnetic radiation reflected from, or transmitted through, a skin region of a subject's body;

a heart rate sensing means; and a processor, operatively coupled with the sensing interface and heart rate sensing means and adapted to:

derive at least two pulse signals, each formed from a weighted combination of the detection signals, wherein weightings for each pulse signal are based on components of a different one of a set of at least two blood volume pulse vectors;

derive a quality indicator value for each derived pulse signal, the quality indicator value being based on a characteristic of a derived relationship between the pulse signal and a heart rate signal of the subject, the heart rate signal being sensed by the heart rate sensing means; and derive physiological information indicative of at least one physiological parameter from the blood volume pulse vector resulting in the pulse signal having the highest quality indicator value and/or from the derived pulse signal itself.

The invention is based on the advantageous integration of sensor information from an auxiliary heart rate sensing means into the physiological parameter sensing method to achieve improved physiological parameter sensing. In particular, a more robust quality assessment of the blood volume pulse vectors can be performed, thereby realizing more reliable selection of the blood volume pulse vector which will yield the most accurate determination of the physiological parameter information.

The general concept with regards determining the quality indicator value may be understood as determining the degree to which each derived pulse signal corresponds with or contains components of the subject's heart rate, as represented by a heart rate signal derived from a heart rate sensing means. Greater correspondence may indicate greater signal to noise ratio, which may indicate less distortion by motion artefacts.

The characteristic of the derived relationship may refer to a strength of a relationship between the derived pulse signal and the measured heart rate signal.

The blood volume pulse vectors may otherwise be referred to as blood volume vectors, or signature vectors.

The blood volume pulse vectors ('$P_{bv}$ vectors') are similar to those referred to above in relation to the APBV method. These are vectors whose components represent possible relative pulsatilities of optical signals at two or three different wavelength components. In particular, the method involves deriving a plurality of pulse-signals where each is formed as a combination (e.g. linear combination) of the detection signals, using weightings correlated with one of the set of blood volume pulse vectors. The vectors in this context are hence not vectors in a spatial co-ordinate system but rather vectors of a self-constructed 'blood volume pulse' space. The blood volume pulse vectors may be a predetermined set of vectors, or the vectors may be constructed by the processor in real-time. This will be described in greater detail below.

The heart rate sensing means may sense either heart rate or pulse rate without consequence on the efficacy of the method. For simplicity and brevity, in the following disclosure embodiments will be described with reference to use of a 'heart rate signal' derived from the heart rate sensing means. However, in all cases, a pulse rate signal may instead be measured and used.

Furthermore, for the following disclosure, the term 'heart rate signal' is to be understood as referring to a signal derived from the heart rate sensing means, i.e. a direct measurement of the subject's 'true' heart rate or pulse rate. By contrast, 'pulse signal' unless stated otherwise is to be understood as referring to a derived pulse signal, as derived in accordance with the method of the invention based on one of the set of blood volume pulse vectors.

The term 'reflected from' is to be understood as covering the case in which light is scattered from a skin region of the subject, e.g. scattered from blood within such a skin region, in addition to cases in which it is reflected in a classical sense from a surface or substance.

Each blood volume pulse vector may contain n components. The n components of each blood volume pulse vector represent possible relative pulsatilities in each of the n detection signals Cn, where the n detection signals may for instance derive from different frequency (or color) channels of the sensing interface, each sensing a particular part of the reflected or transmitted electromagnetic radiation spectrum.

By relative pulsatilities is meant in general the relative strength of a blood pulse in each of the three detection signal channels, i.e. effectively the relative strength of each of the three detection signals.

For a given subject, in the absence of motion or other artefacts or distortions, there will typically be a relatively stable blood volume pulse vector $P_{bv}$ which accurately represents the strength of each of the set of n detection signals when a measurement is taken, e.g. representing the relative pulsatility in each of the n color channels. From this can be derived physiological parameter information such as SpO2, pulse rate, CO and $CO_2$.

However, motion of a subject, physical displacement of the sensing interface or other interference can lead to distortion in the obtained detection signals, which leads to deviation from the 'true' non-distorted (signature) blood volume pulse vector for a subject. Some of the detection signals will for instance increase in relative strength, thereby leading to a distortion in the ratio between the various channel strength values. However, these changes in strength are due to noise in the signal(s), rather than a true reflection of a change in underlying physiological parameters. The problem is how to identify variations in the color channel signals caused by noise, and variations caused by genuine physiological changes.

The solution of the so-called adaptive $P_{bv}$ (APBV) method of which this invention is a development is to effectively construct a plurality of prospective pulse signals, each formed from a weighted combination of the detection signals, and then to test each pulse signal using a quality assessment to determine which achieves the greatest 'quality indicator value'. This quality indicator value may directly or indirectly be indicative of signal to noise ratio for instance.

The detection signals are weighted for each generated prospective pulse signal based on relative sizes of components of one of a set of prospective blood volume pulse vectors. In this way, a set of potential pulse signals is generated, each being correlated with one of the set of different blood volume pulse vectors. The derived pulse signal having the highest quality indicator value indicates that the blood volume pulse vector upon which it was based is most accurately representative of the 'true' (non-distorted) blood volume pulse vector for that subject, in the absence of noise and distortions which may be affecting the raw detection signals.

The innovation of the present invention is to advantageously incorporate additional heart rate sensor data into the quality assessment to achieve a more (motion) robust, and so more reliable, quality assessment of the various prospective pulse signals. Each derived pulse signal is, in accordance with this method, assessed relative to a real-time acquired physiological parameter, improving therefore the accuracy and robustness.

More particularly, the quality indicator is derived for each pulse signal, based on a characteristic of a derived relationship between the measured heart rate signal and each derived pulse signal.

The characteristic of the derived relationship may refer to strength of a relationship between the pulse signal and the heart rate signal.

The characteristic of the derived relationship may refer to a degree of correlation between the pulse signal and the heart rate signal.

The characteristic of the derived relationship may refer to a strength of frequency component(s) in the pulse signal corresponding to frequency components of the heart rate signal of the subject.

As indicated above, greater correspondence with the measured heart rate signal may indicate greater signal to noise ratio of the pulse signal (relative to the physiological pulse), which may indicate less distortion by motion artefacts, and hence more accurate representation of the true, undistorted pulse signal.

The sensing interface may comprise a photoplethysmography (PPG) sensing means. The sensing interface may be a PPG sensor.

The sensing interface may comprise a chest-mountable sensing unit. This may for instance be a chest patch. The chest-mountable sensing unit may incorporate or comprise a PPG sensor. In examples, the chest-mountable sensing unit may conveniently also comprise or incorporate the heart rate sensing means. This is convenient for both the subject (who does not need an additional sensing element to be coupled to them) and for the clinician, who need only affix or mount one sensing unit to the subject.

The heartrate sensing means may in examples be a separate heartrate sensing element or device (separate from the sensing interface), or may be comprised by or integral with the sensing interface.

According to one set of embodiments, the heartrate sensing means may comprise an ECG sensing means and/or an accelerometer.

An ECG sensing means refers to an electrocardiogram means or device. The ECG sensing means may comprise one or more sensors adapted for application against the skin for detecting electrical signals produced by the subject's heart each time it beats. In this way, heart rate can be derived.

ECG carries the advantage of high motion robustness.

An accelerometer provides a highly convenient means for measuring heart rate and is based on use of motion data, e.g. vibrations caused by heartbeats. Motion based heart rate sensing may be advantageously applied in examples for patients suffering from significant arrhythmias. Here, the object of the invention is less connected with improved motion robustness, and more connected with improved performance on patients with such arrhythmias.

For patients with severe arrhythmias, determining the highest quality pulse signal is particularly difficult. This is because the standard approach to identifying the quality indicator is simply to take the height of the highest peak of the frequency spectrum of each pulse signal as the value of the quality indicator. However, for patients with severe arrhythmias, the frequency spectrum of each pulse signal is generally very disperse, making identification of a single 'highest' peak difficult, or at least an unreliable indicator of the signal's quality.

Hence, in these cases, accuracy of results is improved by use of an auxiliary heart rate sensing means (as in the present invention) which allows determination of the true pulse frequency, so that the quality indicator can be more reliably determined as the height of the peak corresponding to the particular heart rate frequency(ies).

In accordance with one or more embodiments, the heart rate sensing means may comprise a photoplethysmography, PPG, sensing means. Measurement of a heart rate signal using a PPG sensor is a well-known procedure in the art.

In these cases, the heart rate sensing means may in particular examples be integral with the sensing interface and wherein both comprise the same photoplethysmography, PPG, sensing means. In these cases, the heart rate sensing means is comprised by the sensing interface, and the same single PPG sensor facilitates the functions of both the sensing interface and the heart rate sensing means.

In these examples, the PPG sensor may be adapted to radiate and sense electromagnetic radiation of a plurality of wavelengths, and wherein one subset of wavelengths is used for obtaining the at least two detection signals, and a further subset of wavelengths is used for obtaining the heart rate signal. The two subsets of wavelengths may overlap to some extent in particular examples.

In particular, examples, the heart rate sensing means may be integral with the sensing interface and wherein both comprise the same photoplethysmography, PPG, sensing means.

By 'integral with' may for instance mean that the heart rate sensing means is comprised by the sensing interface, that the heart rate sensing means is one and the same as the sensing interface and/or that the two are facilitated by the same device or component, i.e. in this case the same PPG sensing means.

The system may be for sensing blood analyte concentration parameters.

The physiological parameter sensed by the system may be blood oxygen saturation, SpO2. The system may in this case be an oxygen saturation sensing system. $SpO_2$ is one example of a blood analyte concentration parameter.

In this case, deriving the physiological information indicative of the physiological parameter, i.e. of SpO2, may comprise, as discussed above, use of a pre-determined lookup table which associates $P_{bv}$ vectors with $SpO_2$ values. Alternatively, a calibration equation may be used, allowing determination of $SpO_2$ based on the $P_{bv}$ vector. A calibration equation might for instance take the form $SpO_2 = 100 - C_1 * k$ where $C_1$ is a detection signal value received from the $SpO_2$ sensor and k is number associated with the $P_{bv}$ vector which yields the highest quality signal (e.g. a number of the $P_{bv}$ vector as listed in a table or list).

However, other physiological parameters may also be derived, for instance the concentrations of carboxyhemoglobin, methemoglobin and bilirubin. These are each also examples of blood analyte concentration parameters.

The physiological parameter is in each case preferably derived from the determined blood volume pulse vector. This can be performed in a similar manner as for deriving $SpO_2$. However, the pulse signal with the best quality indicator value itself is also an interesting physiological parameter which can according to the invention be processed and output by the system. Even further, the pulse-rate, inter-beat interval, or heart-rate variability can be derived from said pulse signal. This pulse signal may be more robust in case of varying SpO2 than a pulse signal obtained with a fixed blood volume pulse vector.

In accordance with examples, the set of blood volume pulse vectors may be pre-determined.

For example, the system, e.g. the controller of the system, may comprise a memory and the blood volume pulse vectors may be pre-stored on the memory. In other examples, they may be stored remotely and accessed via a communication channel established with the remote data store.

In this case, the processor may be configured to use a fixed set of blood volume pulse vectors, i.e. each blood volume pulse vector corresponds to a discrete physiological parameter value, e.g. SpO2 value. For instance, the fixed set of vectors may represent SpO2 values in the range 60% to 100%, with e.g. 10 different vectors covering the range.

In accordance with any embodiment, the processor may be adapted to generate output information indicative or representative of the derived physiological information indicative of at least one physiological parameter. The processor may further be adapted to communicate this generated output information via a communication channel to a locally connected or remotely connected computer, processor or data store for instance.

In accordance with examples, the quality indicator value for each derived pulse signal may be related to a strength of one or more frequency components of the heart rate signal within a frequency spectrum of the pulse signal.

Strength is intended to be construed broadly, meaning any metric which is indicative of the degree to which a frequency component is present in the pulse signal.

The quality indicator value for each derived pulse signal may be indicative of a signal to noise ratio of the respective pulse signal relative to the patient's true heart rate. This gives a good indication of the quality of the blood volume pulse vector for deriving physiological parameters for the patient based on the particular optical signal reading they have given.

In examples, the quality indicator value for each derived pulse signal may be derived based on a value of one or more frequency components of the pulse signal corresponding to frequency components of the heart rate signal.

By value is meant e.g. size, magnitude or height of the frequency component (rather than e.g. the frequency it represents).

For example, each pulse signal may be transformed into the frequency domain, e.g. through a Fourier transform. The value of the relevant frequency components may then be determined.

In examples, the quality indicator value may be taken to be the height of the frequency spectrum peak substantially or exactly at the measured heart rate frequency, i.e. the value of the signal, when transformed in the frequency domain, corresponding exactly or substantially to the measured heart rate frequency (or frequencies where a heart rate spectrum is obtained for instance). Other frequencies components may in this case be ignored.

In examples the heart rate signal may comprise just one frequency component, or may comprise a plurality of components. In examples, just the strongest (i.e. largest) frequency component of the heart rate signal may be selected, and only this component identified and selected within the pulse signal spectrum.

In examples, the quality indicator value for each pulse signal may be taken to be the highest maximum value in a frequency spectrum for the pulse signal, i.e. the value or height of the highest peak in a frequency spectrum for the pulse signal. By value in this context is meant magnitude or 'peak height'.

This approach is based on an assumption that the highest peak in the frequency spectrum of each pulse signal corresponds to, or is caused by, the subject's physiological blood pulse. The value or height of this frequency component, i.e. its strength within the frequency domain, gives an indication of the signal to noise ratio. Hence, by using the height ofthe highest peak as the quality indicator value, an indicator is chosen which is representative of the SNR each pulse signal corresponding to the subject's physiological pulse.

In accordance with one or more examples of this approach, deriving the quality indicator value may comprise enhancing in each pulse signal one or more frequency components corresponding to frequency components of the heart rate signal in advance of determining the quality indicator. The height of the highest peak in the frequency spectrum of the pulse signal is then selected as the quality indicator value for each pulse signal.

This better ensures that the highest peak indeed corresponds to the subject's pulse, since those one or more frequency components matching the heart rate signal one or more components are augmented.

Additionally or alternatively, in examples of this approach, deriving the quality indicator value for each pulse signal may comprise suppressing or eliminating frequency components of the pulse signal not corresponding to frequency components of the heart rate signal in advance of determining the quality indicator. The height of the highest peak in the frequency spectrum of the pulse signal is then selected as the quality indicator value for each pulse signal.

This again better ensures that the highest peak does correspond to the subject's pulse, as components not matching components known to be present in the heart rate signal are either diminished or removed.

In accordance with an alternative set of embodiments, the deriving the quality indicator value for each derived pulse signal may be based on determining a strength of correlation between the pulse signal and the heart rate signal, or a signal derived from the heart rate signal.

This represents an alternative approach to determining a strength of relationship between each derived pulse signal and the heart rate signal for the subject. This gives a means for assessing signal to noise ratio of the pulse signal in relation to the subject's true pulse. The stronger the correlation, the greater the strength of the signal component(s) in the derived pulse signal corresponding to the subject's pulse.

By 'strength' of correlation is generally meant the degree of correlation, i.e. for instance the value of a correlation coefficient determined between the respective pulse signal and the heart rate signal.

In examples of this approach, deriving the quality indicator value for each pulse signal comprises applying a Hilbert transform to the pulse signal to derive an analytical signal, and subsequently deriving a strength of correlation between the analytical signal and the heart rate signal for the subject.

When using the pulse-signal itself to derive the correlation, the correlation may be sensitive to phase shifts between the heart rate signal sensed by the heart rate sensing means and the PPG-derived pulse signal. By using instead a derived analytical signal, it is possible to determine a correlation which is independent of (or unaffected by) any phase-shift between the two. In particular, this approach allows deriving of both a magnitude of the correlation and also the phase difference, where the phase difference can then be neglected.

In accordance with one or more sets of embodiments, the processor may be adapted, in advance of deriving the at least two pulse signals, to perform a filtering step in which the obtained detection signals are adaptively filtered to reduce the contribution of signal components caused by motion.

In examples, this may comprise filtering based on a motion signal obtained from a motion sensor coupled to the subject. In particular, the detection signals may be filtered to reduce or eliminate frequency components identified in the frequency spectrum of the motion signal. In other examples, the filtering may be based on the heart rate signal derived from the heart rate sensing means. In this case, the detection signals may be filtered to reduce or eliminate frequency components not identified in the heart rate signal.

This reduces the potential contribution of subject motion in deriving the physiological parameter information, thereby reducing potential inaccuracy in measurement results.

A band-pass filter may be used in particular examples, where the range of frequencies passed is selected based on frequency components detected in the frequency spectrum of the heart rate signal derived using the heart rate sensing means.

Examples in accordance with a further aspect of the invention provide a physiological parameter sensing method comprising:

obtaining at least two detection signals derived from detected electromagnetic radiation reflected from, or transmitted through, a skin region of a subject's body;

obtaining a heart rate signal for the subject;

deriving at least two pulse signals, each formed from a weighted combination of the detection signals, wherein weightings for each pulse signal are based on components of a different one of a set of at least two blood volume pulse vectors;

deriving a quality indicator value for each derived pulse signal, the quality indicator value being based on a characteristic of a derived relationship between the pulse signal and the heart rate signal of the subject; and deriving physiological information indicative of at least one physiological parameter from the blood volume pulse vector resulting in the pulse signal having the highest quality indicator value and/or from the derived pulse value itself.

Examples in accordance with a further aspect of the invention provide a computer program product comprising computer program code, adapted, when run on a computer, to cause the computer to carry out any embodiment of the physiological parameter sensing method outlined above.

BRIEF DESCRIPTION OF THE DRAWINGS

Preferred embodiments of the invention will now be described in detail, by way of example only, with reference to the accompanying drawings, in which.

DETAILED DESCRIPTION OF THE EMBODIMENTS

The invention provides a physiological parameter sensing system and method in which information indicative of at least one physiological parameter is derived. The approach of the invention is based on constructing multiple pulse signals from different weighted combinations of at least two detection signals, derived from detected electromagnetic radiation directed onto or through a subject's skin region. The weightings are based on different of a set of various blood volume pulse vectors. A quality indication value is derived for each generated pulse signal, where this is based on a derived relationship between an obtained heart rate signal for the patient and the pulse signal. The blood volume pulse vector resulting in the pulse signal having the highest quality indicator value and/or from the derived pulse signal itself is used to derive the physiological parameter information.

Figure 4:
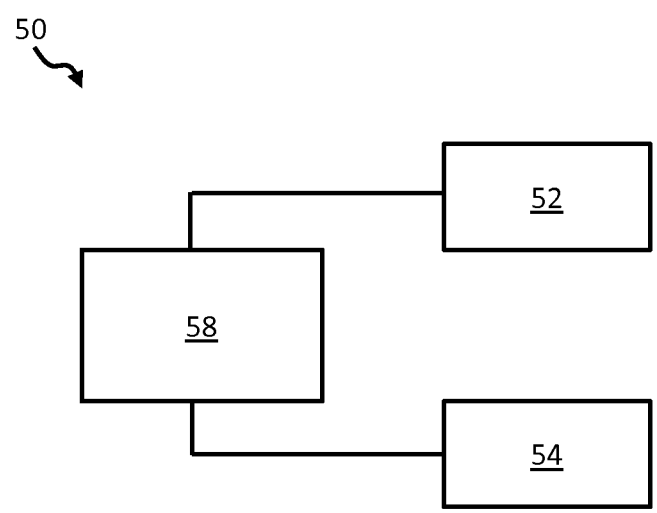
FIG. 4 schematically depicts a sensing system in accordance with one or more embodiments of the invention.

FIG. 4 shows a block diagram of an example physiological parameter sensing system in accordance with one or more embodiments of the invention. The system 50 comprises a sensing interface 52 adapted to obtain at least two detection signals Cn derived from detected electromagnetic radiation reflected from, or transmitted through, a skin region of a subject's body. In the example of FIG. 4, the sensing interface comprises a PPG (photoplethysmography) sensor.

The different detection signals Cn correspond to different wavelengths of radiation. In certain examples, either two or three detection signals may be obtained for two or three wavelengths of light. Advantageously, these may wavelengths (selected from) e.g. 660 nm 810 nm and 940 nm.

The system 50 further comprises a heart rate sensing means 54 for obtaining a heart rate signal from the subject indicative of the subject's heart or pulse rate.

In preferred examples, the heart rate sensing means comprises either an ECG sensing device or a motion sensing device, such as an accelerometer.

An ECG sensing device may comprise electrodes or other sensors for application or attachment to a subject's body for sensing electrical signals generated by the heart. These signals allow the beating of the heart, and hence heart rate, to be detected.

Where an accelerometer is used, heart rate may be detected based on motion sensing, for instance sensing vibrations around the chest area of the patient, or sensing movements of the chest caused by beating of the heart.

Further details of motion-based heart rate sensing are found in document U.S. Pat. No. 9,510,775.

Other heart rate sensing means may alternatively be used, such as ultrasound based sensing means and inductive sensing means.

The heart rate sensing means may in accordance with some examples comprise, or be facilitated by, a PPG sensor. Sensing heart rate (or pulse rate) using a PPG sensor is a well-known procedure and is discussed above.

The sensing interface 52 and heart rate sensing means 54 are operatively coupled to a processor 58 which is adapted to process sensing signals obtained by each of the interface and sensing means and to generate therefrom physiological information indicative of one or more physiological parameters of a subject.

In one advantageous set of embodiments, at least one of the sensing interface 52 and the heart rate sensing means 54 is integrated within a chest-mountable sensing unit, e.g. a chest patch. Even more preferably, both the sensing interface and heart rate sensing means are integrated in such a chest-mountable sensing unit.

Figure 5:
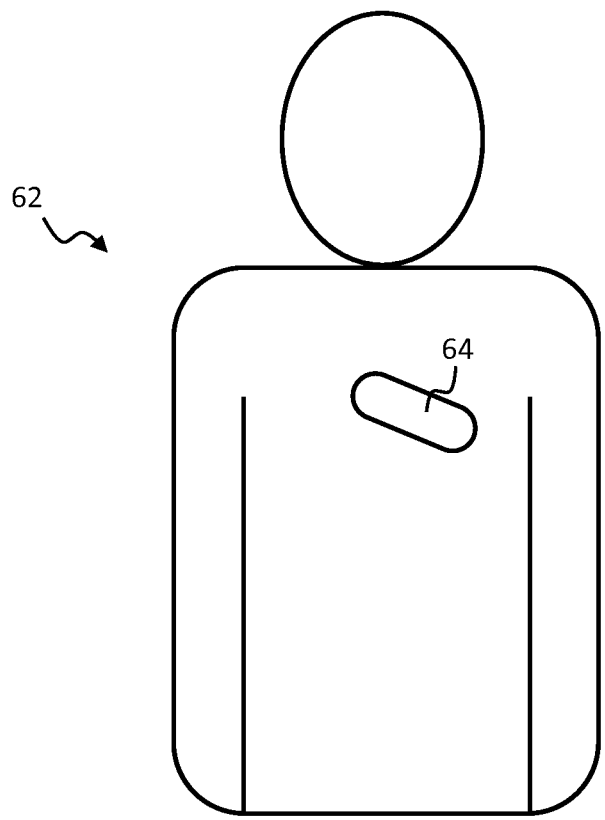
FIG. 5 schematically illustrates an example chest patch integrating a sensing interface and heart rate sensing means as may be used in accordance with one or more embodiments of the invention.

An example is schematically illustrated in FIG. 5 which shows a subject 62 wearing a chest patch 64 incorporating, by way of example, an integrated PPG sensor and ECG sensor. Additionally or alternatively, in examples, the patch may incorporate one or more of: a thermometer and a motion sensor such as an accelerometer. The motion sensor may in examples be used for measuring respiration rate and/or context information such as body posture, and whether or not a subject is walking.

A chest-mounted sensor device may be particularly useful for patients in a general ward of a hospital or in skilled nursing facilities for instance. A chest patch-based sensing unit such as in FIG. 5 is convenient for the subject as he or she can remain fully mobile, without ceasing the collection of physiological data.

Although in the example of FIGS. 4 and 5, the sensing interface comprises a PPG sensor, any sensing device may be used operable to apply electromagnetic radiation to a skin region of a subject's body and to detect the reflection or transmission of the radiation from or through the subject's body.

In general, any combination of an electromagnetic radiation emitter (e.g. an LED) and an electromagnetic radiation sensor (e.g. a photo-diode, or sensor array) may be used. Plural different electromagnetic radiation emitters (emitting different wavelengths) may be used. These may be used for instance in time or frequency multiplex. In other examples, a broad-band emitter may be combined with a sensor-array having optical filters applied to individual cells in order to simultaneously sense radiation reflected or transmitted from the skin.

Although in the example outlined above, a separate sensing interface 52 and heart rate sensing means 54 are provided, in alternative examples, the two may be integral with one another, as will be described in greater detail below.

Where a subject is mobile, there is an increased risk of motion artefacts in derived physiological parameter information.

The present invention is aimed at providing a more motion-robust measurement method for deriving physiological parameter information.

As discussed above, the invention is a development of a previous method for deriving physiological information indicative of physiological parameters. This method is described in detail in WO 2017/055218 and will be referred to as the 'adaptive PBV' method (APBV method).

Embodiments of the invention improve the robustness of the APBV method by utilizing additional sensor data related to the subject's cardiac activity (i.e. through the heart rate sensing means 54).

The processor is configured to process signal data from the sensing interface 52 and heart rate sensing means in accordance with the improved algorithm to derive the physiological parameter information.

To better understand the present invention, a discussion of the principles of the known APBV method will now be outlined. Greater detail may be found in WO 2017/055218, in G. de Haan and A. van Leest, "Improved motion robustness of remote-PPG by using the blood volume pulse signature", Physiol. Meas. 35 1913, and in M. van Gastel, Sander Stuijk, and G. de Haan, "New principle for measuring arterial blood oxygenation, enabling motion-robust remote monitoring", Scientific Reports 6, Article number: 38609 (2016).

Commonly used methods for measuring physiological parameters such as blood oxygen saturation, SpO2, use a ratio of PPG sensor signal amplitude in red and infrared (IR). Particularly the red PPG signal is very small. With this known method, the amplitude of the red PPG signal is overestimated because it includes noise. In contrast, the APBV method does not base physiological parameter measurements directly upon the sensed light frequency amplitudes, but rather identifies a pulse blood volume ("signature") vector (explained below) which yields a derived pulse signal exhibiting the best signal to noise ratio (SNR)

A PPG signal results from variations of the blood volume in the skin. In particular, the beating of the heart causes pressure variations in the arteries as the heart pumps blood against the resistance of the vascular bed. Since the arteries are elastic, their diameter changes in synchrony with the pressure variations, thereby increasing the local volume of blood present in a given region. These diameter changes occur even in the smaller vessels of the skin, where the volume variations cause a changing absorption of the light.

The variations give rise to a characteristic pulsatility "signature" in terms of relative strengths of different spectral components of the reflected/transmitted light. This signature results from a contrast between the absorption spectra for blood compared with that of the blood-less skin tissue.

If the detector, e.g. a camera or sensor, has a discrete number of color channels Cn, each sensing a particular part of the light spectrum, then the relative pulsatilities (as indicated by signal strength) for these channels can be mathematically represented in the form of a "signature vector", also referred to as the "normalized blood-volume vector", $P_{bv}$. It has been shown in G. de Haan and A. van Leest, "Improved motion robustness of remote-PPG by using the blood volume pulse signature", Physiol. Meas. 35 1913, 2014, that if this signature vector is known then a motion-robust pulse signal extraction on the basis of the color channels and the signature vector is possible.

The unit length normalized blood volume pulse vector (also called signature vector), defined as $P_{bv}$, indicates the relative PPG-strength in the red, green and blue optical signal channels, i.e.

$$\vec{P}_{bv} = \frac{[\sigma(\vec{R}_n), \sigma(\vec{G}_n), \sigma(\vec{B}_n)]}{\sqrt{\sigma^2(\vec{R}_n), \sigma^2(\vec{G}_n), \sigma^2(\vec{B}_n)}}$$

where σ indicated the standard deviation.

To demonstrate the concept, a sample blood volume pulse vector was derived in tests, making use of a remote PPG sensor comprising a camera.

To quantify first the expected $P_{bv}$ vector components, the signal responses $H_{red}(w)$, $H_{green}(w)$ and $H_{blue}(w)$ of the red, green and blue channel, respectively, were measured as a function of the wavelength w, of a global-shutter color CCD camera which would be used to obtain the optical detection signals Cn. The model takes account of the skin reflectance of a subject, $\rho_s(w)$. The values were based on absolute PPG-amplitude curve PPG(w).

Figure 1:
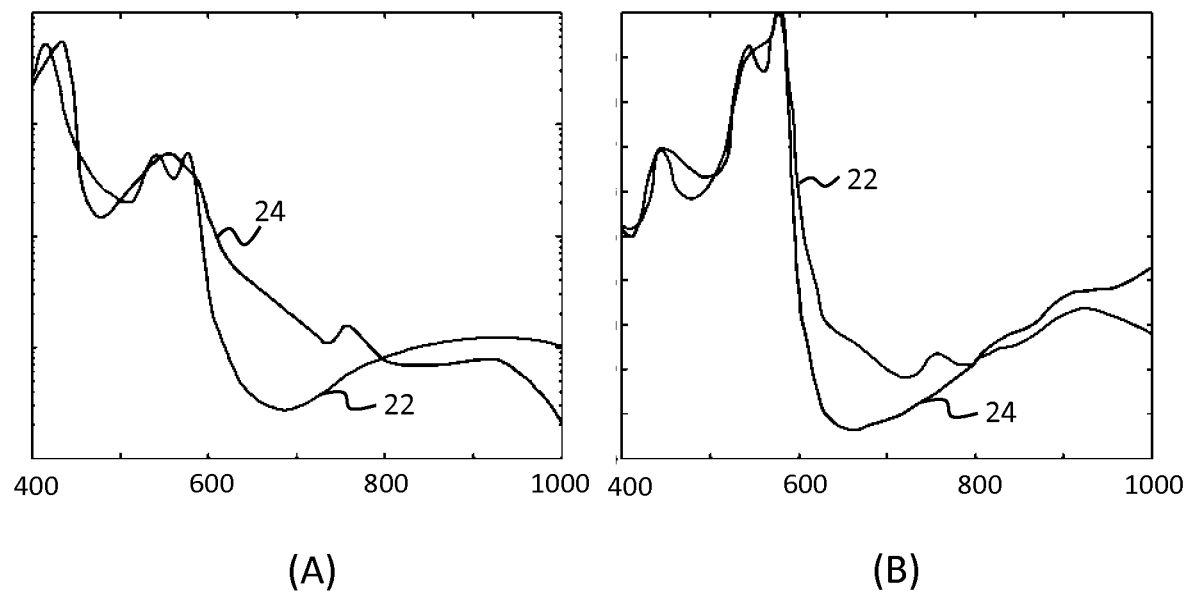
FIG. 1 shows molar extinction coefficients and pulsatilities for partially oxygenated and completely oxygenated blood.
Figure 2:
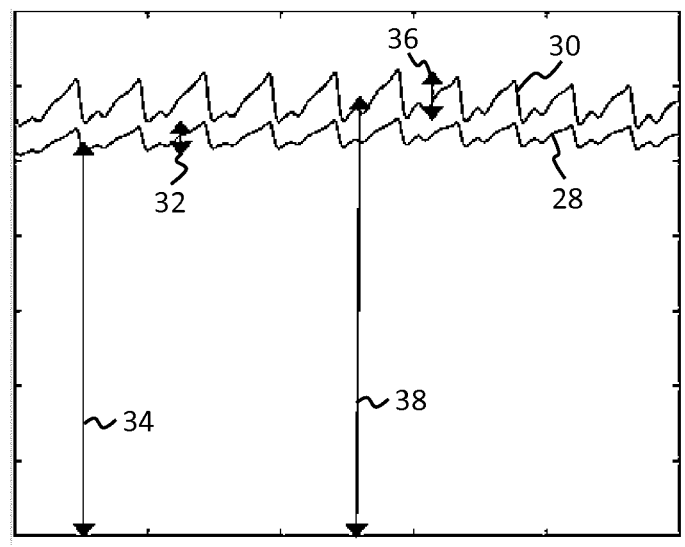
FIG. 2 schematically illustrates AC and DC components of an $SpO_2$ sensor signal.

From these curves, shown e.g. in FIG. 2 of the above cited paper of de Haan and van Leest, the theoretical blood volume pulse vector $P_{bv}$ is computed as:

$$\vec{P}_{bv}^T = \begin{bmatrix} \frac{\int_{w=400}^{700} H_{red}(w)I(w)PPG(w)dw}{\int_{w=400}^{700} H_{red}(w)I(w)\rho_s(w)dw} \\ \frac{\int_{w=400}^{700} H_{green}(w)I(w)PPG(w)dw}{\int_{w=400}^{700} H_{green}(w)I(w)\rho_s(w)dw} \\ \frac{\int_{w=400}^{700} H_{blue}(w)I(w)PPG(w)dw}{\int_{w=400}^{700} H_{green}(w)I(w)\rho_s(w)dw} \end{bmatrix}$$

which, using a white, halogen illumination spectrum I(w), leads to a normalized $P_{bv}$=[0.27, 0.80, 0.54]. When using a more noisy curve, the result may be $P_{bv}$=[0.29, 0.81, 0.50].

These values were obtained for healthy subjects having a known SpO$_2$ value of 98+/−2%.

The blood volume pulse predicted by the used model corresponds reasonably well to the experimentally measured normalized blood volume pulse vector, $P_{bv}$=[0.33, 0.78, 0.53] found after averaging measurements on a number of healthy subjects under white illumination conditions, and having the same known SpO$_2$. Given this result, it was concluded that the observed PPG-amplitude, particularly in the red, and to a smaller extent in the blue channel, can be largely explained by the crosstalk from wavelengths in the interval between 500 and 600 nm. The precise blood volume pulse vector depends on the color filters of the camera or optical sensor, the spectrum of the light and the skin-reflectance, as the model shows. In practice, the vector turns out to be fairly stable for a given set of wavelength channels (the vector will be different in the infrared compared to RGB-based vector).

It has further been found that the relative reflectance of the skin, in the red, green and blue channel under white illumination does not depend much on the skin-type.

Consequently, it has been concluded that the normalized blood volume pulse vector $P_{bv}$ is very stable under constant, e.g. white, illumination for a given constant SpO2.

The stable character of the blood volume pulse vector $P_{bv}$ enables it therefore to be usefully used in distinguishing between color variations in an obtained signal caused by blood volume changes and variations due to alternative causes such as motion of the subject or movement of the sensor, i.e. the $P_{bv}$ vector can be used as a "signature" of blood volume change so as to distinguish such changes from other causes of color variations.

The known relative pulsatilities of the color channels $P_{bv}$ can thus be used to discriminate between components of the derived pulse signal representative of true physiological pulse-signal and those caused by distortions.

In accordance with the APBV method, each derived pulse signal S may in examples be written as a linear combination (or another kind of "mixing") of the individual DC-free normalized color channels:

$$S = W C_n$$

with $WW^T = 1$ and where each of the three rows of the 3×N matrix $C_n$ contains N samples of the DC-free normalized red, green and blue channel signals $R_n$, $G_n$ and $B_n$, respectively, i.e.:

$$\vec{R}_n = \frac{1}{\mu(\vec{R})}\vec{R} - 1, \vec{G}_n = \frac{1}{\mu(\vec{G})}\vec{G} - 1, \vec{B}_n = \frac{1}{\mu(\vec{B})}\vec{B} - 1$$

The operator μ corresponds to the mean.

The APBV method obtains the mixing coefficients, W, using the blood volume pulse vector, as described for instance in US 2013/271591 A1 and also the above cited paper of de Haan and van Leest. Best results are obtained if the band-pass filtered versions of $R_n$, $G_n$ and $B_n$ are used. According to this method the known 'direction' of $P_{bv}$ (in detection-signal channel space) may be used to discriminate between the pulse signal and distortions.

A pulse signal is derived as a linear combination of normalized color signals. Since it is known that the relative amplitude of the pulse signal in the red, green and blue channel is given by $P_{bv}$, the weights, $W_{PBV}$, are searched that give a pulse signal S, for which the correlation with the color channels $R_n$, $G_n$, and $B_n$ equals $P_{bv}$. In other words a weighted combination of at least two detection signals is sought using weights selected such that the resulting pulse signal correlates with the original detection signals $C_n$ and with the pulse blood volume ($P_{bv}$) vector.

and consequently the weights for the mixing are determined by $$\vec{S} C_n^T = k\vec{P}_{bv} \Leftrightarrow \vec{W}_{PBV} C_n C_n^T = k\vec{P}_{bv}$$

and consequently the weights for the mixing are determined by $$\vec{W}_{PBV} = k\vec{P}_{bv} Q^{-1} \text{ with } Q = C_n C_n^T$$

where the scalar k is determined such that $W_{PBV}$ has unit length. It is concluded that the characteristic wavelength dependency of the PPG signal, as reflected in the normalized blood volume pulse $P_{bv}$ can be used to estimate the pulse signal from the time-sequential RGB pixel data averaged over the skin area.

Hence, as explained above, a pulse signal (S1, S2) may be derived as a weighted sum of the at least two detection signals $C_n$.

However, to achieve an 'accurate', i.e. noise free, pulse signal, it is important that the signature used to create the pulse signal is 'correct', i.e. accurately representative of the true blood volume variations, as otherwise the weightings applied will mix noise into the generated pulse signal.

To this end, in the APBV method, quality indicator values are computed for each of the derived pulse signals, and the physiological information indicative of at least one physiological parameter is derived only using the signature vector) that results in the pulse signal with the best quality indicator value and/or from said pulse signal, i.e. from the pulse signal with the best quality indicator value.

It is known that if detection signals are combined according to simply an arbitrary ratio, the resulting pulse signal will exhibit a relatively poor signal-to-noise (SNR) ratio, (i.e. a poor quality indicator). Hence, by choosing in advantageous embodiments, the blood volume pulse vector $P_{bv}$ which gives the best SNR pulse signal (i.e. the best quality indicator), the algorithm gets closest to realizing the correct physiological parameter information (e.g. the blood oxygen saturation, $SpO_2$).

Hence the APBV-method uses a quality criterion to steer the selection of the optimal pulse volume blood vector $P_{bv}$ vector.

Figure 3:
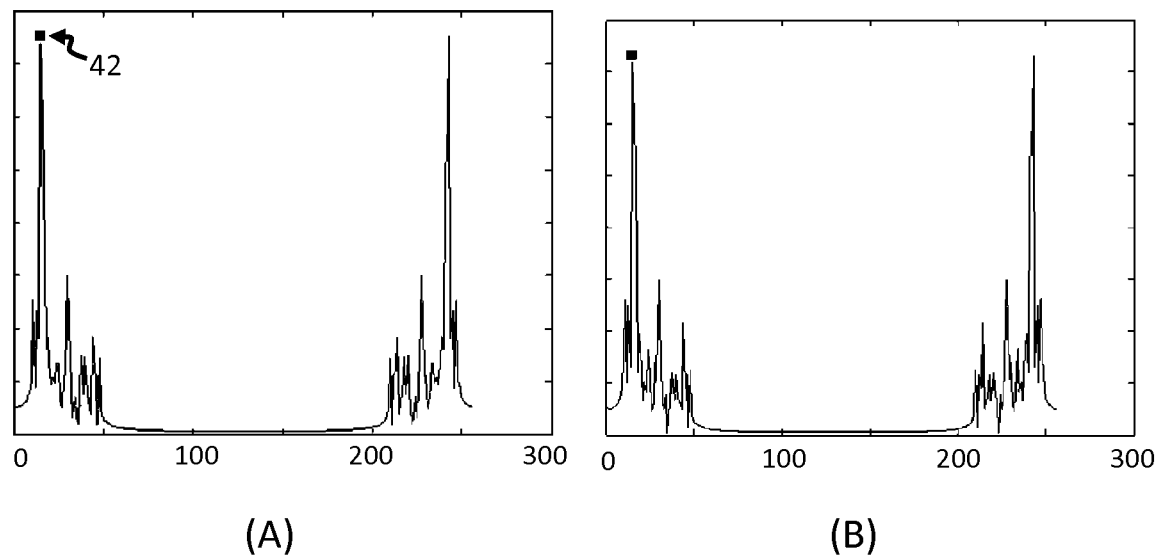
FIG. 3 shows frequency spectra for two sample pulse signals derived from different blood volume vectors.

An example implementation for determining a best quality $P_{bv}$ vector was illustrated above with reference to FIG. 3 for instance.

The extracted pulse-signal is transformed into the Fourier (frequency) domain and the resulting spectrum is normalized (sum of spectral energies equals 1).

The height of the highest peak is used as the quality indicator value. For the method to work, it is necessary that the highest peak in the spectrum is indicative of the subject's pulse and is not for instance noise caused by motion. Hence, although the method works well for static patients in controlled conditions, for mobile patients, there is a risk that motion could lead to creation of a large component of noise in the signal, distorting the selection of the $P_{bv}$ vector.

This problem is addressed in the present invention through use of heart-rate information obtained from another (more motion-robust) sensor to improve the accuracy of determined physiological parameter information.

In accordance with one set of embodiments of the invention, a frequency spectrum of a subject's cardiac activity is measured using the heart rate sensing means 54 (e.g. an ECG-sensor or accelerometer). Following this, the frequency components identified within the obtained heart rate signal spectrum are enhanced or augmented within the derived pulse signal spectrum prior to identifying the highest spectral peak. In this way, it is better ensured that the highest peak within the spectrum does in fact correspond to the subject's pulse. Hence, the value (i.e. height) of the highest peak is rendered a more robust quality indicator metric.

In accordance with a further set of embodiments, again a frequency spectrum of the subject's heart rate signal is obtained using the heart rate sensing means 54. Following this, the frequency components of the Fourier-transformed pulse signal not corresponding to the frequency components identified in the obtained heart rate signal spectrum are diminished or eliminated prior to identifying the highest spectral peak. Again, this better ensures that the highest peak within the spectrum does in fact correspond to the subject's pulse, and so ensures the highest peak height is a more robust quality indicator metric.

In accordance with one set of embodiments, a frequency spectrum of the subject's cardiac activity is again obtained using the heart rate sensing means 54. Following this, the quality indicator value is determined based on the signal value or height of the Fourier-transformed pulse-signal only at frequencies corresponding to frequency components identified in the heart rate signal spectrum.

For example, the quality indicator value may be taken to be the value of the highest peak within the Fourier-transformed pulse signal corresponding to a frequency component of the heart rate signal. Alternatively, the quality indicator value may be taken to be the average height of all of the peak heights in the pulse signal spectrum corresponding to frequency components of the heart rate signal.

In accordance with an alternative set of embodiments, the quality indicator value may be based on a strength of correlation between the pulse signal and the heart rate signal as derived using the heart rate sensing device. In alternative examples, the quality indicator value may be based on a strength of correlation between the respective frequency spectra for the pulse signal and the heart rate signal. In other words, the quality indicator value may be based on a strength of correlation between the pulse signal and the heart rate signal as derived either in the time domain or the frequency domain.

In accordance with this set of embodiments, a correlation may first derived or calculated between each derived pulse signal and the obtained heart rate signal, for instance by deriving the standard Pearson coefficient between the two signals. The quality indicator value for each pulse signal may then for instance simply be taken as the derived correlation coefficient itself.

In accordance with an advantageous set of examples, an analytic signal may first be derived from the heart rate signal, using for instance the Hilbert Transform. The quality indicator value for each pulse signal may then be based on the magnitude of correlation between the pulse signal and the derived analytical signal. The quality indicator may for instance simply be taken as said magnitude of correlation itself Once a quality indicator value has been derived for each derived pulse signal, these values are compared and the pulse signal having the highest quality indicator value is identified. Following this, physiological information indicative of at least one physiological parameter is derived either from the blood volume pulse vector $P_{bv}$ from which the highest quality pulse signal was derived, or from the highest quality pulse signal itself In accordance with one set of embodiments, information indicative of blood oxygen saturation $SpO_2$ is derived.

As explained above, SpO2 may in examples be derived from the identified highest quality $P_{bv}$ vector by means of a pre-determined lookup table which associates $P_{bv}$ vectors with $SpO_2$ values, or in alternative examples by means of a calibration equation allowing determination of $SpO_2$ based on the $P_{bv}$ vector. A calibration equation might for instance take the form $SpO_2=100-C_1*k$ where $C_1$ is a detection signal value received from the $SpO_2$ sensor and k is number associated with the $P_{bv}$ vector which yields the highest quality signal (e.g. a number of the $P_{bv}$ vector as listed in a table or list).

Additionally or alternatively, information indicative of other physiological parameters may be derived from the highest quality pulse signal and/or the corresponding blood volume pulse vector $P_{bv}$. Physiological parameters which could be derived include for instance carboxyhemoglobin (CO bound to hemoglobin), bilirubin and methemoglobin.

These could be derived from the identified highest quality $P_{bv}$ vector in a similar manner to SpO2, by means of dedicated pre-determined lookup tables allowing association of the $P_{bv}$ vectors with the physiological parameters, or by means of dedicated correlation equations.

As discussed above, in the APBV method, pulse signals are derived from weighted combinations of detection signals Cn, each pertaining to a different wavelength of radiation (e.g. different color channel of detected light), where the weightings are based on components of different of a set of $P_{bv}$ vectors. The same approach is applied in the present invention.

In particular, the processor 58 may computes at least two pulse signals S1, S2 from said at least two detection signals Cn using different (normalized) blood volume vectors $P_{bv}1$, $P_{bv}2$, for the computation of each pulse signal. This step is explained in detail for instance in the above cited paper of de Haan and van Leest or in M. van Gastel, S. Stuijk and G. de Haan, "Motion robust remote-PPG in infrared", IEEE, Tr. On Biomedical Engineering, 2015.

The different blood volume vectors $P_{bv}1$, $P_{bv}2$ used for the computation of each pulse signal provide an expected relative strength of the pulse signal S1, S2 in the at least two detection signals Cn. The computation of a pulse signal S1, S2 involves a weighted combination of the at least two detection signals Cn using weights selected such that the resulting pulse signal S1, S2 correlates with the original detection signals Cn as indicated by the respective signature vector $P_{bv}1$, $P_{bv}2$, e.g. correlates with the original detection signals in a proportionality dictated by the $P_{bv}$ vector components.

In more detail, the processor 58 may be configured to compute the pulse signals by computing a co-variance matrix $Q=C_n C_n^T$ of normalized DC-free detection signals Cn over a time window and find the weights $W_x$ to compute a pulse signal $S_x = \vec{W}_x C_n$ as $$\vec{W}_x = k\vec{P}_{bv}Q^{-1}$$

where k is chosen such that $\|\vec{W}_x\|=1$ and $x \in \{1, 2\}$. It should be noted that the weights and the blood volume pulse vectors $P_{bv}$ are different for the two pulse signals obtained from the same detection signals Cn.

In preferred examples, a fixed set of different blood volume pulse vectors $P_{bv}1$, $P_{bv}2$ is used. These may be pre-determined in examples.

The fixed set of blood volume pulse vectors $P_{bv}1$, $P_{bv}2$ cover the range of the physiological parameter to be measured. For instance, for $SpO_2$, a set of blood volume pulse vectors may correspond to $SpO_2$ values in a range between 60% and 100%. The vectors are the same for every subject and may be stored for instance in a look-up table.

A given set of blood volume vectors typically pertains to measurement of only one variety of physiological parameter. In the present example, $SpO_2$ is being considered. However, if another blood gas is to be determined, a different set of blood volume vectors is necessary (as this other gas gives a different blood-absorption spectrum, depending on the concentration of the gas).

It is assumed for the present illustrative explanation, that only one blood component is to be determined, although, with a sufficiently high number of wavelengths, more than one blood component in principle is measureable, provided the set of signature vectors covers all possible combinations of gasses. The multiple different sets of blood volume vectors may be stored in a lookup table for instance.

The above described processing may be done over a time window, e.g. 10 seconds, of detection signals may be obtained in each wavelength channel. This window may then be a sliding window, i.e. the next measurement is again from a 10 second window, registered somewhat later in time. From the measurements obtained in each window, a physiological parameter (e.g. $SpO_2$) estimate is derived (derived based on the found "best quality" blood volume pulse vector). The resulting succession of physiological parameter estimates (from the different time windows) may then be (temporally) filtered in order to obtain a smoother and higher resolution measurement.

This filtering may be understood as follows.

As discussed, the sensing system may be adapted to obtain detection signals recurrently, for instance at regular time intervals. The processor may be adapted to determine from these a corresponding time-series (succession) of 'highest quality' blood volume pulse vectors, each being a blood volume pulse vector for which a highest quality pulse signal was derived for the given point in time (based on the relevant obtained set of detection signals for that time point). Additionally or alternatively, a corresponding series of physiological parameter measurements (e.g. $SpO_2$) may be derived from the series of $P_{bv}$ vectors.

The processor may in such cases filter the obtained time sequence of blood volume pulse vectors to obtain a filtered signature vector from which physiological information is derived (or the processor may filter the $SpO_2$ values to obtain a filtered $SpO_2$ value).

In particular, the time series of vectors (or values) may be temporally filtered in order to eliminate outliers, or smooth the result, to thereby achieve a more reliable result, or for instance to improve the resolution of the derived physiological parameter (e.g. $SpO_2$).

For example, a filter may be applied which is configured only to retain $P_{bv}$ vectors which correspond to $SpO_2$ values which are no greater than 5% apart. In this case, the temporal filtering may increase the $SpO_2$ resolution to 1%.

In accordance with one or more embodiments, the processor may be configured, in determining a blood volume pulse vector which results in a pulse signal having highest quality, to adapt one or more of a limited set of blood volume pulse vectors (Pbv1, Pbv2) in a direction that depends on which pulse signal yields the best quality indicator value.

In these embodiments, determining a blood volume pulse vector ($P_{bv}$) which results in the highest quality pulse vector may be performed by means of an iterative method, whereby an initial limited set of $P_{bv}$ vectors is tested, and, based on the results, improved $P_{bv}$ vectors are selected or derived for testing until a highest quality $P_{bv}$ vector is converged upon.

In such a method, rather than testing all possible $P_{bv}$ vectors (corresponding to the complete range of relevant physiological parameter values, e.g. SpO2-values), just a limited set, for instance two, are tested. By 'tested' in this context is meant deriving from the relevant $P_{bv}$ vector a pulse signal and determining a quality indicator value for that pulse signal.

By way of example, if upon testing the initial set (e.g. of two) pulse volume vectors, the $P_{bv}$ vector corresponding to the lowest $SpO_2$ value achieves the highest quality indicator value, then a second round of testing commences, wherein that low $SpO_2$ value vector and an even lower value $SpO_2$ $P_{bv}$ vector are tested. This process continues until convergence upon a $P_{bv}$ vector achieving the highest-quality pulse signal is achieved.

In other words, a dynamic iterative process of testing is followed in which results of each round of testing are used to guide the direction in which further testing is to be performed, i.e. whether higher or lower physiological parameter-corresponding $P_{bv}$ vectors should be tested.

The result is a recursive process, which involves fewer computations, and is hence more efficient.

In accordance with one or more sets of embodiments, the processor may be adapted, in advance of deriving the at least two pulse signals, to perform a filtering step in which the obtained detection signals are adaptively filtered to reduce noise. In particular, the detection signals may be filtered to reduce the contribution of signal components caused by motion.

In one set of examples, the sensing system may be adapted to adaptively filter the detection signals based on a reference noise signal. For example, the reference noise signal may be a signal corresponding to a (motion) disturbance affecting the sensing system.

In one particular set of examples for instance, the sensing system may comprise a motion sensing means, for instance an accelerometer, attached or coupled to the subject for sensing the subject's motion. The controller 58 of the system is adapted to obtain a motion signal from the motion sensing means and to adaptively filter the detection signals in accordance with the motion signal. In this case, the motion signal is used as the reference noise signal. For instance, the controller may reduce the magnitude of, or remove, frequency components of the detection signals corresponding to frequency components detected in the obtained motion signal. This may be performed by first transforming the detection signals and the motion signal into the frequency domain.

Figure 6:
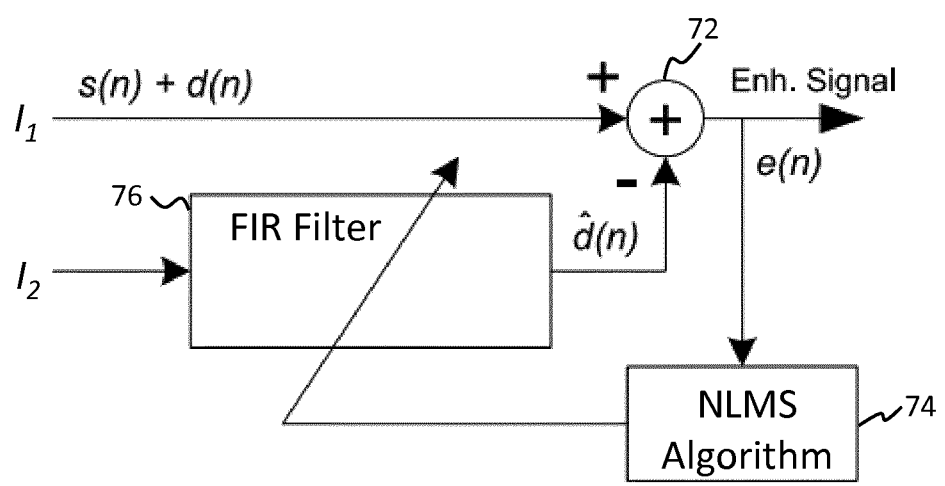
FIG. 6 illustrates a filter circuit for removing noise from obtained detection signals based on a reference signal for the noise.

An example filter circuit for performing such a filtering process is illustrated in FIG. 6. In accordance with the example circuit, an input detection signal $I_n = s(n) + d(n)$ (where s(n) corresponds to the error-free signal and d(n) corresponds to the noise component of the signal) is iteratively processed by an adaptive finite impulse response (FIR) filter 76.

An adaptive filter is a dynamic filter which iteratively alters its filtering characteristics in order to achieve an optimal output. In particular, an adaptive filter is adapted to adjust its parameters based on an algorithm to minimize a function of the difference between a desired output of the filter and the actual output at each iteration.

In the present example, filtering parameters of the adaptive filter 76 are altered based on outputs of a normalized linear mean square (NLMS) algorithm 74. This is a well-known adaptive filter algorithm in the present field, and the person skilled in the art would recognize means for putting it into effect in the context of the illustrated circuit, The circuit iteratively processes the input detection signal $I_n$ with the adaptive filter 76. The adaptive filter receives as input a reference signal $I_2$ corresponding to the noise d(n). For the present example, the reference signal is taken to be an output signal of a motion detector, such as an accelerometer coupled to the subject for measuring motion of the subject. The motion corresponds to motion disturbances which generate noise artefacts in the detection signals. The filter 76 is adapted to reduce the magnitude of, or remove, frequency components of the input signal $I_1$ which correspond to frequency components found in a frequency spectrum of the reference noise signal $I_2$.

The output of the adaptive filter is subtractively combined via a mixer 72 with the input detection signal $I_n$ to derive an error signal e(n).

At each iteration, the error signal e(n) is then fed back into to the NLMS algorithm, and the parameters of the adaptive filter 76 are updated based on the error signal. The error signal is then re-processed with the adaptive filter to further filter noise and iteratively advance to an optimized filtered signal.

The final converged result is output from the filter circuit. This is labelled as an enhanced signal ('Enh. signal') in FIG. 6.

In accordance with a further set of examples, the controller 58 may instead be adapted to filter the detection signals (in advance of deriving the at least two pulse signals) based on a reference signal for the subject's pulse.

In particular, the detection signals may in certain examples be filtered in accordance with the heart rate signal detected by the heart rate sensing means of the sensing system. In these examples, the controller is adapted to obtain a measure of the subject's heart or pulse rate using the heart rate sensing means 54 and to reduce the magnitude of, or remove, frequency components of the detection signals not corresponding to detected frequency components of the measured heart rate signal. The controller may optionally also be adapted to increase the magnitude or relative magnitude of frequency components of the detection signals corresponding to frequency components detected in the measured heart rate signal. This may be performed by first transforming the detection signals and the obtained heart rate signal into the frequency domain.

Figure 7:
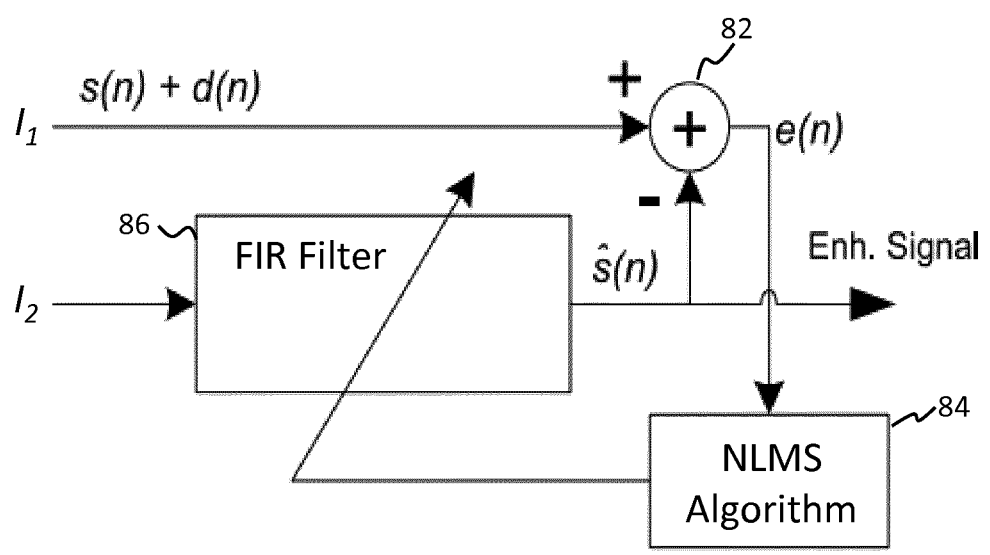
FIG. 7 illustrates a filter circuit for removing noise from obtained detection signals based on a reference pulse signal.

An example filter circuit for performing such a filtering process is illustrated in FIG. 7.

In similarity with the circuit of FIG. 6, the circuit comprises an adaptive finite impulse response (FIR) circuit 86 which is configured to iteratively filter input detection signal $I_n=s(n)+d(n)$ where s(n) is the error free detection signal and d(n) is the error component of the signal.

The adaptive filter receives as input a reference signal $I_2$ corresponding to the subject's pulse. For the present example, the reference signal is taken to be the heart rate signal obtained from the heart rate sensing means of the sensing system. As described in examples above, the heart rate sensing means may in particular examples comprise a PPG sensor or an ECG sensing device. The filter 86 is adapted to reduce the magnitude of, or remove, frequency components of the input signal $I_1$ not corresponding to frequency components found in a frequency spectrum of the reference heart rate signal $I_2$.

The output of the adaptive filter 86 is subtractively combined via a mixer 82 with the input detection signal L to derive an error signal e(n). The error signal is iteratively reprocessed with the adaptive filter 86, wherein parameters of the filter are updated at each iteration according to a normalized linear mean square algorithm 84 (in the same way as described for the circuit of FIG. 6 above) based on the error signal e(n). The final converged result is output from the filter circuit as an enhanced signal ('Enh. signal').

In accordance with a further set of examples, a band-pass frequency filter may be applied to the detection signals in advance of determining the pulse signals (e.g. a narrow band-pass frequency filter). The range of frequencies passed by the filter may in these cases be determined in accordance with detected frequency components of a heart rate signal obtained using the heart rate sensing means. In this case, only those frequency components of the detection signals finding correspondence in the frequency spectrum of the heart rate signal would remain after application of the filter. This represents for instance a simple means for implementing the pre-filtering approach outlined in the example described immediately above.

By filtering the detection signals in advance of deriving the pulse signals, the contribution of motion artefacts can be reduced, thereby enabling improved accuracy in physiological parameter measurements.

As noted above, embodiments of the invention may advantageously make use of a chest patch comprising or integrating the sensing interface (e.g. $SpO_2$ sensor) and the heart rate sensing means (e.g. an ECG or accelerometer). In this way, all sensors may be conveniently integrated in the single patch. Such a patch should give accurate SpO2 readings even for mobile subjects (e.g. general ward patients and skilled nursing facility patients or residents).

More broadly, any $SpO_2$ sensor whether chest patch based or not may in examples benefit from the solutions provided by this invention.

Another example of an application for which the invention may provide benefits is that of contactless physiological parameter monitoring, e.g. using with a camera (vital signs camera), such as remote PPG sensing.

As noted briefly above, the heart rate sensing means may be facilitated in a number of different ways.

In accordance with various embodiments, the heart rate sensing means may comprise, or may be facilitated by, a PPG sensor. The PPG sensor in some cases may be applied to a different location of the body to the sensing interface used to derive the detection signals used for determining the physiological parameter information.

In one set of embodiments for instance, the sensing system may comprise a single auxiliary PPG sensor for sensing a heart rate or pulse rate of the subject. By way of a simple example, a patient may for instance be continuously monitored with an auxiliary PPG sensor (e.g. a finger PPG sensor) which is adapted to continuously or recurrently derive a heart rate signal (in the form of a pulse rate). A physiological parameter sensing system (e.g. a bilirubinometer, for optically sensing bilirubin levels), may comprise a sensing interface and processor, and may be adapted to communicatively connect to the PPG sensor for receiving the sensed heart rate signal outputs. The communicative connection may for instance comprise a near field communication (NFC) connection, Bluetooth connection or any other wired or wireless communication channel or link.

A sensing interface of the bilirubinometer is used by the processor to derive physiological information indicative of bilirubin in accordance with the method of the invention, utilizing the heart rate signal information obtained from the PPG sensor.

In accordance with a further example set of embodiments, the sensing system may comprise a plurality of PPG sensors for sensing heart rate signals. In some examples, the strength of the heart rate signal obtained from each may be determined, and the single sensor realizing the highest strength heart rate signal (e.g. the highest signal to noise ratio) may be used for obtaining the heart rate signal used in deriving the physiological parameter information in accordance with the method of the invention.

In one simple example for instance, multiple $SpO_2$ sensors (which are examples of a PPG sensor) may be applied simultaneously at different locations on a patient's body. Each $SpO_2$ sensor is operable to sense both heart rate and to obtain detection signals Cn for deriving SpO2 in accordance with the method of the invention. In this case, each SpO2 sensor performs the function of both the sensing interface 52 and the heart rate sensor 54 (i.e. the two are integral with one another).

The sensor identified as generating the strongest measured heart rate signal (in the form of measured pulse signal) (e.g. highest signal-to-noise ratio) is then identified. This sensor is then used as the heart rate sensing means for all of the other sensors in deriving $SpO_2$ (or any other physiological parameter) in accordance with the invention.

In accordance with at least one set of embodiments, both the heart rate sensing means and the sensing interface may comprise or be facilitated by a PPG sensor. In such cases, the two may be integrally combined, i.e. both may comprise or be facilitated by the same PPG sensor.

In these cases, the single PPG sensor may be adapted to radiate and sense electromagnetic radiation of multiple different wavelengths, and wherein one subset of the wavelengths is used for directly detecting a heart rate signal (or pulse rate signal) and a further subset of wavelengths is used for obtaining the detection signals used for obtaining the physiological parameter measurements in accordance with the method of the invention.

In one set of examples, a single PPG sensing means may be utilized, adapted to emit and to sense electromagnetic radiation of at least three different wavelengths, for instance 520 nm (green), 660 nm (red), 830 nm (infrared) and optionally also 940 nm (infrared). The PPG sensing means may in particular examples be incorporated into a chest patch, or wrist band, or may be provided by a camera (i.e. a remote PPG sensing means).

The green light alone may be used to measure the heart rate signal for use in the method of the invention, while the red and infrared light are used to obtain the detection signals for use in deriving the physiological parameter information (e.g. $SpO_2$). The green PPG signal typically has much higher signal-to-noise ratio (stronger pulse, higher AC/DC) than red and infrared and is thus more suitable for determining the heart or pulse rate. Furthermore, green light has a more shallow penetration depth into tissue and is therefore less suitable for determining SpO2 for instance than red and infrared light.

In accordance with a further set of examples, a single PPG sensing means may be utilized, adapted to emit and to sense electromagnetic radiation of at least two different wavelengths, for instance 520 nm (green), and one or more red and/or infrared wavelengths.

The green light alone may be used to measure the heart rate signal for use in the method of the invention, while the signal of the green light may be used together with the red/infrared light for obtaining the detection signals for use in deriving the physiological parameter information, such as $SpO_2$. Again, the PPG sensing means may in examples be incorporated into a chest patch, or wrist band, or may be provided by a camera (i.e. a remote PPG sensing means).

In accordance with a further set of examples, a single PPG sensing means may be utilized, adapted to emit and to sense electromagnetic radiation of at least three different wavelengths, for instance 520 nm (green), 660 nm (red), 830 nm (infrared) and optionally also 940 nm (infrared). The PPG sensing means may in examples be incorporated into a chest patch, or wrist band, or may be provided by a camera (i.e. a remote PPG sensing means).

The heart rate signal for use in the method of the invention may be obtained using a combination of the wavelengths (green together with red and/or infrared). This can be achieved using the method described in the paper "Improved motion robustness of remote-PPG by using the blood volume pulse signature", de Haan, G and van Leest, A. This method is similar to the method used in the present invention and comprises deriving a plurality of different prospective pulse signals based on different weighted combinations of the different color channel signals (green, red and/or infrared), the weightings determined based on components of a set of pulse volume vectors. A quality indicator value is determined for each derived pulse signal (e.g. signal to noise ratio), and the pulse signal having the highest quality indicator value is used as the auxiliary heart rate signal in determining the physiological parameter in accordance with the invention.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A physiological parameter sensing system, comprising:
a sensing interface adapted to obtain at least two detection signals derived from detected electromagnetic radiation reflected from, or transmitted through, a skin region of a subject's body;
means for sensing a heart rate; and
a processor, operatively coupled with the sensing interface and the means for sensing the heart rate and adapted to:
control the means for sensing the heart rate to acquire a heart rate signal, the heart rate signal being distinct from the detection signals;
derive at least two pulse signals, each formed from a weighted combination of the detection signals, wherein weightings for each pulse signal are based on components of a different one of a set of at least two blood volume pulse vectors;
derive, using the heart rate signal, a quality indicator value for each derived pulse signal, the quality indicator value being based on a characteristic of a derived relationship between the pulse signal and the heart rate signal of the subject; and
derive physiological information indicative of at least one physiological parameter from the blood volume pulse vector resulting in the pulse signal having the highest quality indicator value and/or from the derived pulse signal having the highest quality indicator value,
wherein the quality indicator value for each derived pulse signal is derived based on:
a value of one or more frequency components of the pulse signal corresponding to a frequency component of the heart rate signal, and/or determining a strength of correlation between the pulse signal and the heart rate signal or a signal derived from the heart rate signal.

2. The physiological parameter sensing system as claimed in claim 1, wherein the sensing interface comprises a photoplethysmography (PPG) sensor.

3. The physiological parameter sensing system as claimed in claim 2, wherein the means for sensing the heart rate is integral with the sensing interface.

4. The physiological parameter sensing system as claimed in claim 1, wherein the means for sensing the heart rate comprises an ECG sensor and/or an accelerometer.

5. The physiological parameter sensing system as claimed in claim 1, wherein the means for sensing the heart rate comprises a photoplethysmography (PPG) sensor.

6. The physiological parameter sensing system as claimed in claim 1, wherein the sensing interface comprises a chest-mountable sensing unit.

7. The physiological parameter sensing system as claimed in claim 6, wherein the chest mountable sensing unit comprises a PPG sensor and the means for sensing the heart rate.

8. The physiological parameter sensing system as claimed in claim 1, wherein the physiological parameter is blood oxygen saturation (SPO2) and the system is an oxygen saturation sensing system.

9. The physiological parameter sensing system as claimed in claim 1, wherein deriving the quality indicator value comprises enhancing in each pulse signal one or more frequency components corresponding to frequency components of the heart rate signal in advance of determining the quality indicator, and
wherein the quality indicator value for each pulse signal is taken to be the value of the highest maximum value in a frequency spectrum for the pulse signal.

10. The physiological parameter sensing system as claimed in claim 9, wherein deriving the quality indicator value for each pulse signal comprises suppressing or eliminating frequency components of the pulse signal not corresponding to frequency components of the heart rate signal in advance of determining the quality indicator.

11. The physiological parameter sensing system as claimed in claim 1, wherein deriving the quality indicator value for each pulse signal comprises applying a Hilbert transform to the pulse signal to derive an analytical signal, and subsequently deriving a strength of correlation between the analytic signal and the heart rate signal for the subject.

12. A physiological parameter sensing method comprising:
   obtaining at least two detection signals derived from detected electromagnetic radiation reflected from, or transmitted through, a skin region of a subject's body;
   obtaining a heart rate signal for the subject, different from the detection signals;
   deriving at least two pulse signals, each formed from a weighted combination of the detection signals, wherein weightings for each pulse signal are based on components of a different one of a set of at least two blood volume pulse vectors;
   deriving, using the heart rate signal, a quality indicator value for each derived pulse signal, the quality indicator value being based on a characteristic of a derived relationship between the pulse signal and the heart rate signal of the subject, wherein the deriving the quality indicator value for each derived pulse signal comprises determining a value of one or more frequency components of the pulse signal corresponding to a frequency component of the heart rate signal, and/or determining a strength of correlation between the pulse signal and the heart rate signal or a signal derived from the heart rate signal; and
   deriving physiological information indicative of at least one physiological parameter from the blood volume pulse vector resulting in the pulse signal having the highest quality indicator value and/or from the derived pulse value having the highest quality indicator value.

13. A non-transitory computer readable medium storing instructions that, when executed by one or more processors, cause the one or more processors to perform the method of claim 12.

14. The physiological parameter sensing method as claimed in claim 12, wherein the quality indicator value for each derived pulse signal is derived based on a value of one or more frequency components of the pulse signal corresponding to frequency components of the heart rate signal.

15. The physiological parameter sensing method as claimed in claim 12, wherein deriving the quality indicator value comprises enhancing in each pulse signal one or more frequency components corresponding to frequency components of the heart rate signal in advance of determining the quality indicator, and wherein the quality indicator value for each pulse signal is taken to be the value of the highest maximum value in a frequency spectrum for the pulse signal.

16. The physiological parameter sensing method as claimed in claim 12, wherein deriving the quality indicator value for each pulse signal comprises suppressing or eliminating frequency components of the pulse signal not corresponding to frequency components of the heart rate signal in advance of determining the quality indicator.

17. The physiological parameter sensing method as claimed in claim 12, wherein the deriving the quality indicator value for each derived pulse signal is based on determining a strength of correlation between the pulse signal and the heart rate signal, or a signal derived from the heart rate signal.

18. The physiological parameter sensing method as claimed in claim 12, wherein deriving the quality indicator value for each pulse signal comprises applying a Hilbert transform to the pulse signal to derive an analytical signal, and subsequently deriving a strength of correlation between the analytic signal and the heart rate signal for the subject.

19. A physiological parameter sensing system, comprising:
   a sensing interface adapted to obtain at least two detection signals derived from detected electromagnetic radiation reflected from, or transmitted through, a skin region of a subject's body;
   a heart rate sensor; and
   a processor, operatively coupled with the sensing interface and the heart rate sensor and adapted to:
   control the heart rate sensor to acquire a heart rate signal, the heart rate signal being distinct from the detection signals;
   derive at least two pulse signals, each formed from a weighted combination of the detection signals, wherein weightings for each pulse signal are based on components of a different one of a set of at least two blood volume pulse vectors;
   derive, using the heart rate signal, a quality indicator value for each derived pulse signal, the quality indicator value being based on a characteristic of a derived relationship between the pulse signal and the heart rate signal of the subject; and
   derive physiological information indicative of at least one physiological parameter from the blood volume pulse vector resulting in the pulse signal having the highest quality indicator value and/or from the derived pulse signal having the highest quality indicator value,
   wherein the quality indicator value for each derived pulse signal is derived based on:
   a value of one or more frequency components of the pulse signal corresponding to a frequency component of the heart rate signal, and/or determining a strength of correlation between the pulse signal and the heart rate signal or a signal derived from the heart rate signal.

20. The physiological parameter sensing system as claimed in claim 19, wherein the sensing interface comprises a chest-mountable sensing unit.

21. The physiological parameter sensing system as claimed in claim 19, wherein deriving the quality indicator value comprises enhancing in each pulse signal one or more frequency components corresponding to frequency components of the heart rate signal in advance of determining the quality indicator, and
   wherein the quality indicator value for each pulse signal is taken to be the value of the highest maximum value in a frequency spectrum for the pulse signal.

22. The physiological parameter sensing system as claimed in claim 21, wherein deriving the quality indicator value for each pulse signal comprises suppressing or eliminating frequency components of the pulse signal not corresponding to frequency components of the heart rate signal in advance of determining the quality indicator.

23. The physiological parameter sensing system as claimed in claim 19, wherein deriving the quality indicator value for each pulse signal comprises applying a Hilbert transform to the pulse signal to derive an analytical signal, and subsequently deriving a strength of correlation between the analytic signal and the heart rate signal for the subject.

* * * * *